US008353839B2

(12) United States Patent
Scheirer et al.

(10) Patent No.: US 8,353,839 B2
(45) Date of Patent: Jan. 15, 2013

(54) INTRACAVITY PROBE WITH CONTINUOUS SHIELDING OF ACOUSTIC WINDOW

(75) Inventors: Barry Scheirer, McAlisterville, PA (US); Kevin Wickline, Yeagertown, PA (US); David Becker, Lewistown, PA (US); Jeffrey Hart, Port Royal, PA (US); Alan Hornberger, McAlisterville, PA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1707 days.

(21) Appl. No.: 10/599,322

(22) PCT Filed: Mar. 22, 2005
(Under 37 CFR 1.47)

(86) PCT No.: PCT/IB2005/050987
§ 371 (c)(1),
(2), (4) Date: Sep. 25, 2006

(87) PCT Pub. No.: WO2005/096267
PCT Pub. Date: Oct. 13, 2005

(65) Prior Publication Data

US 2008/0228082 A1 Sep. 18, 2008

Related U.S. Application Data

(60) Provisional application No. 60/559,388, filed on Apr. 2, 2004, provisional application No. 60/559,321, filed on Apr. 2, 2004, provisional application No. 60/559,390, filed on Apr. 2, 2004.

(51) Int. Cl.
*A61B 8/14* (2006.01)

(52) U.S. Cl. ......................... 600/459; 600/463; 310/335

(58) Field of Classification Search .................. 600/459, 600/463; 29/25.35; 128/661.08, 662.03; 310/335
See application file for complete search history.

(56) References Cited

U.S. PATENT DOCUMENTS

| | | | | |
|---|---|---|---|---|
| 4,802,458 | A * | 2/1989 | Finsterwald et al. | 600/454 |
| 4,807,634 | A | 2/1989 | Enjoji et al. | |
| 5,311,095 | A * | 5/1994 | Smith et al. | 310/334 |
| 5,488,954 | A * | 2/1996 | Sleva et al. | 600/459 |
| 5,531,119 | A | 7/1996 | Meyers | |
| 6,182,341 | B1 * | 2/2001 | Talbot et al. | 29/25.35 |

FOREIGN PATENT DOCUMENTS

| | | | |
|---|---|---|---|
| EP | 0527651 | A | 2/1993 |
| EP | 1501331 | A | 1/2005 |
| JP | 2003309890 | A | 10/2003 |

* cited by examiner

*Primary Examiner* — Brian Casler
*Assistant Examiner* — Joseph M Santos

(57) ABSTRACT

An ultrasound probe has a transducer array which is moved to scan a patient with ultrasonic energy. The array is located in a fluid chamber (42) which is enclosed by an acoustic window end cap (34). The acoustic window cap is coated with a thin conductive layer (38) which shields the transducer and its motive mechanism from EFI/RFI emissions. The conductive layer is coupled to a reference potential.

15 Claims, 4 Drawing Sheets

INTRACAVITY PROBE WITH CONTINUOUS SHIELDING OF ACOUSTIC WINDOW

CROSS REFERENCE TO RELATED APPLICATION

This application claims the benefit of U.S. provisional application Ser. No. 60/559,388 filed Apr. 2, 2004, which is incorporated herein.

This invention relates to medical diagnostic imaging systems and, in particular, to diagnostic ultrasonic imaging probes with continuous shielding of the acoustic window.

Medical ultrasound products are regulated by strict guidelines for radiated emissions (EMI/RFI) to prevent interference with other equipment and to preserve the integrity of the ultrasound image for patient diagnosis. Electronic emissions from ultrasound equipment could interfere with the operation of other sensitive equipment in a hospital. RFI from other instruments such as electrocautery apparatus in a surgical suite can create noise and interference in the ultrasound image and measurements. Accordingly it is desirable to shield the electronics of an ultrasound system and its probes from EMI/RFI emissions to and from these components.

A typical method of making an EMI/RFI shield for an ultrasound probe consists of thin metal layers placed on, in, or in close proximity to the electronic components of the probe and cable, which are appropriately grounded. To shield the front of the transducer, thin metal layers may be located on or around or embedded in the transducer lens material. While these techniques are fairly straightforward for electronic probes with no moving parts, they are much more difficult to apply to probes with mechanically oscillated transducers. The motion of the moving transducer can create gaps in the continuity of the shielding, admitting and allowing emissions around the moving mechanism. Accordingly it is desirable to have an effective shielding technique that will completely shield emissions to and from the moving transducer and its motive mechanism.

In accordance with the principles of the present invention, a mechanical ultrasound probe is described in which the moving transducer is completely shielded from EMI/RFI emissions. The moving transducer is contained within a fluid-filled compartment at the distal end of the probe which is sealed with an acoustic window cap. The cap is lined with a thin, electrically conductive layer that is electrically connected to a reference potential. The conductive layer is sufficiently electrically conductive to provide EMI/RFI shielding, and thin enough to enable the passage of acoustic energy through the acoustic window. The electrically conductive layer may be a continuous surface or a grid-like pattern that provides sufficient shielding for the probe.

Figure 1:
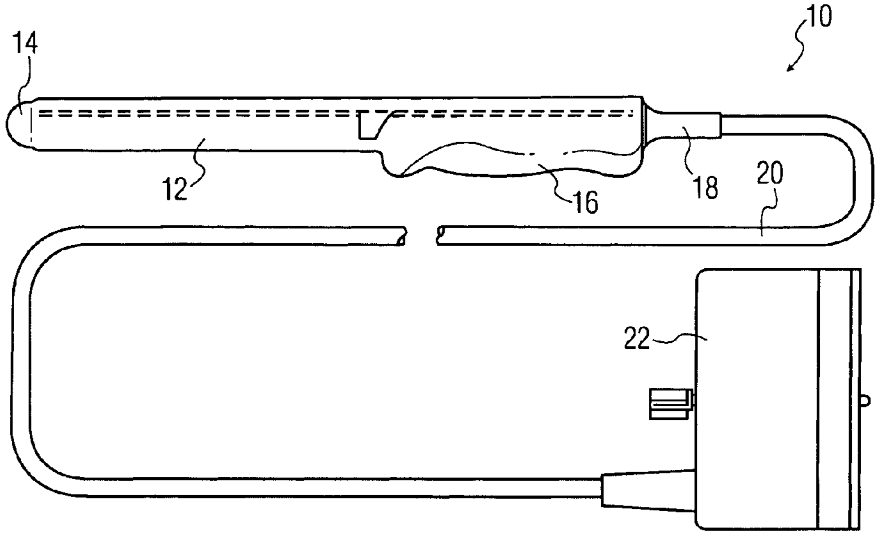
FIG. 1 illustrates a typical intracavity ultrasound probe of the prior art.

In the past, intra-vaginal transducer (IVT) probes and intracavity (ICT) probes have been developed to scan a two dimensional image region from within the body. This could be done with an array transducer or oscillating single crystal transducer which would scan a sector-shaped area of the body. By curving the elements of an array transducer completely around the distal tip region of the probe, sectors approximating 180° could be scanned. A typical IVT intracavity probe 10 is shown in FIG. 1. This probe includes a shaft portion 12 of about 6.6 inches (16.7 cm) in length and one inch in diameter which is inserted into a body cavity. The ultrasound transducer is located in the distal tip 14 of the shaft. The probe is grasped and manipulated by a handle 16 during use. At the end of the handle is a strain relief 18 for a cable 20 which extend about 3-7 feet and terminates at a connector 22 which couples the probe to an ultrasound system. A typical IVT probe may have a shaft and handle which is 12 inches in length and weigh about 48 ounces (150 grams) including the cable 20 and the connector 22.

Figure 2:
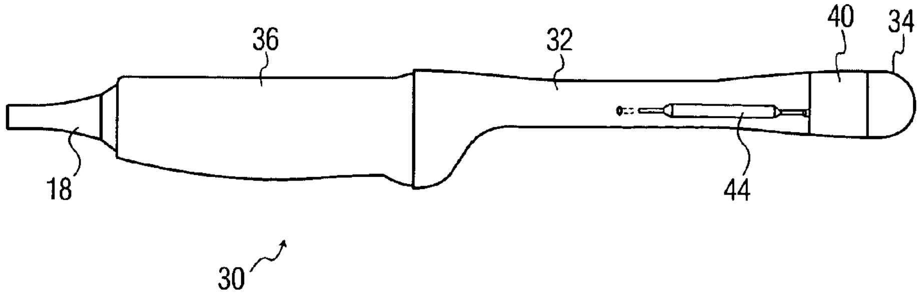
FIG. 2 illustrates a side view of a mechanical intracavity probe for three dimensional imaging which is constructed in accordance with the principles of the present invention.
Figure 3:
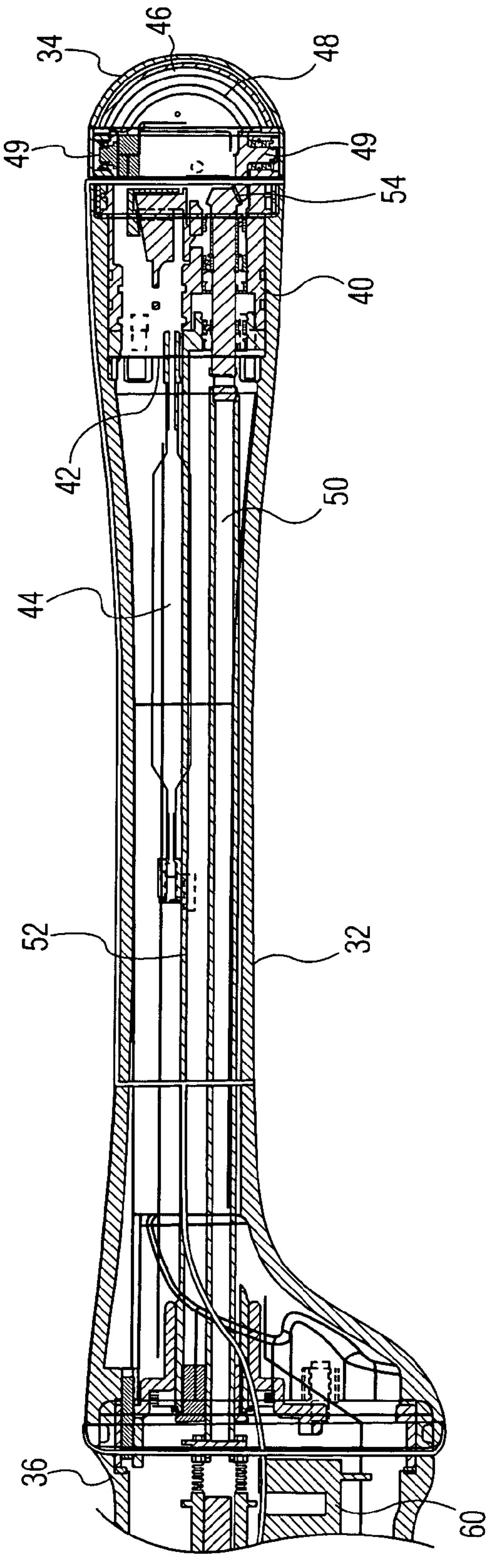
FIG. 3 is a side cross-sectional view of a mechanical intracavity probe constructed in accordance with the principles of the present invention.

Referring now to FIG. 2, an intracavity ultrasound probe 30 for three dimensional imaging which is constructed in accordance with the present invention is shown. The probe 30 includes a handle section 36 by which the user holds the probe for manipulation during use. At the rear of the handle is a strain relief 18 for the probe cable (not shown). Extending from the forward end of the handle 36 is the shaft 32 of the probe which terminates in a dome-shaped acoustic window 34 at the distal end through which ultrasound is transmitted and received during imaging. Contained within the distal end of the shaft is a transducer mount assembly 40 which is also shown in the cross-sectional view of FIG. 3. A convex curved array transducer 46 is attached to a transducer cradle 48 at the distal end of the assembly 40. The transducer cradle 48 is pivotally mounted by a shaft 49 so it can be rocked back and forth in the distal end of the probe and thereby sweep an image plane through a volumetric region in front of the probe. The transducer cradle 48 is rocked by an oscillating drive shaft 50 which extends from a motor and shaft encoder 60 in the handle 36 to a gear 54 of the transducer cradle. The drive shaft 50 extends through an isolation tube 52 in the shaft which serves to isolate the moving drive shaft from the electrical conductors and volume compensation balloon 44 located in the shaft proximal the transducer mount assembly 40. The construction and operation of the rocking mechanism for the transducer cradle 48 is more fully described in concurrently filed US patent application Ser. No. 10/599,306, entitled ULTRASONIC INTRACAVITY PROBE FOR 3D IMAGING, the contents of which are incorporated herein by reference. The echo signals acquired by the transducer array 46 are beamformed, detected, and rendered by the ultrasound system to form a three dimensional image of the volumetric region scanned by the probe.

Because ultrasonic energy does not efficiently pass through air, the array transducer 46 is surrounded by a liquid which is transmissive of ultrasound and closely matches the acoustic impedance of the body which is approximately that of water. The liquid is contained within a fluid chamber 42 inside the transducer mount assembly 40 which also contains the array transducer 46. Water-based, oil-based, and synthetic polymeric liquids may be used. In a constructed embodiment silicone oil is used as the acoustic coupling fluid in the transducer fluid chamber. Further details of the fluid chamber of the embodiment of FIG. 2 may be found in concurrently filed US patent application Ser. No. 10/599,317, entitled ULTRA- SOUND PROBE WITH MULTIPLE FLUID CHAMBERS, the contents of which are incorporated herein by reference.

Figure 4:
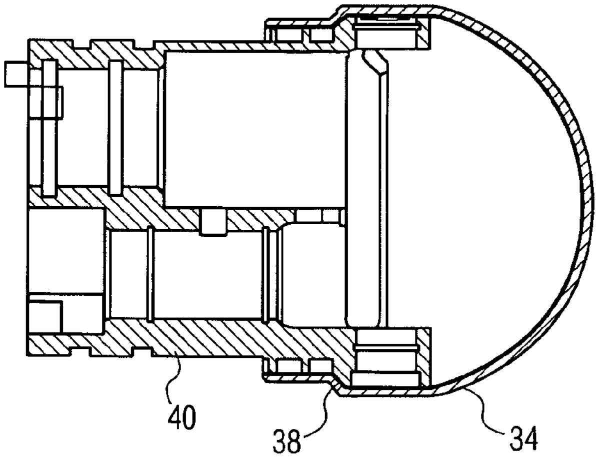
FIG. 4 is a side cross-sectional view of the distal tip of a mechanical intracavity probe constructed in accordance with the principles of the present invention.

In accordance with the principles of the present invention the acoustic window 34 is lined with a thin conductive layer 38 as shown in FIG. 4. The dome-shaped acoustic window 34 is made of a flexible plastic material which makes good contact with the body of a patient and resists cracking in the event the probe is dropped. In a constructed embodiment the acoustic window 34 is made of a polyethylene polymer. A suitable material for the conductive layer 38 is gold, which flexes well on the flexible dome-shaped acoustic window and which tends to self-heal any small fissures which may develop from flexure of the dome. Titanium/gold alloys and aluminum are also suitable candidates for the shielding material. While the conductive layer may be embedded in the acoustic window, it is easier to form the thin layer by vacuum deposition processes such as sputtering, vacuum evaporation, physical vapor deposition, arc vapor deposition, ion plating or laminating. Prior to deposition the polymeric dome can be coated with parylene for better adhesion of the conductive layer. These processes enable the thickness of the layer to be carefully controlled, as it is desirable to have a thin layer which is acoustically transparent at the operating frequency of the transducer. The conductive layer should be thick enough to be electrically conductive, yet thin enough so as not to substantially impede the transmission of ultrasonic energy through the acoustic window. Acoustic transparency was achieved in a constructed embodiment by keeping the thickness of the layer 38 to 1/16 of a wavelength (λ) or less at the nominal operating frequency of the transducer (6 MHz.) In the constructed embodiment the conductive layer 38 had a thickness of 1000-3000 Angstroms or 0.004-0.012 mils which is well within this criterion. A gold layer of 2000 Angstroms (0.00787 mils) and an aluminum layer of 10,000 Angstroms (0.03937 mils) can generally be readily achieved. For most applications with most suitable materials, a conductive layer thickness of 1/128 of a wavelength (~20,000 Angstroms) can generally be obtained with good effect.

Figure 5:
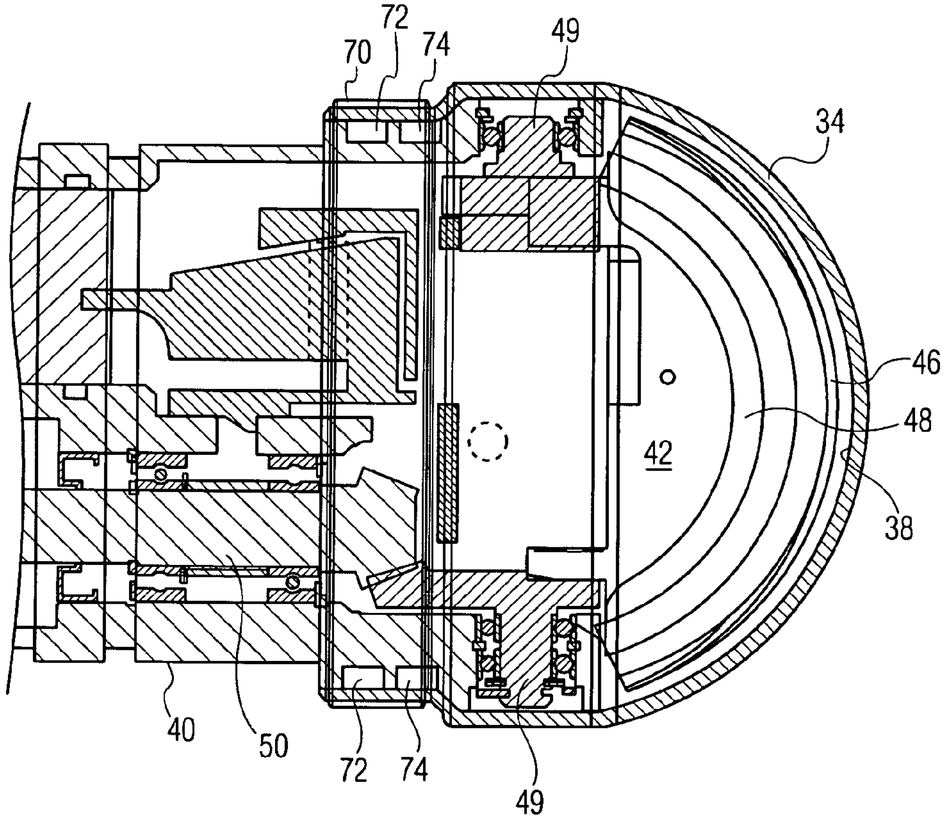
FIG. 5 is an enlarged, more detailed view of the distal probe tip of FIG. 4.

To complete the electrical path for the shielding conductive layer 38 the acoustic window cap 34 is sealed over the distal end of the transducer mount assembly 40 by a metal dome ring 70, shown in FIG. 5. The conductive layer 38 on the inner surface of the acoustic window cap 34 is thereby compressed against two conductive, silver-filled O-rings located in grooves 72 and 74 around the circumference of the assembly 40. The transducer mount assembly in a constructed embodiment is made of aluminum and is grounded, thereby completing the electrical path from the shielding layer 38, through the conductive O-rings, and to the assembly 40 which is at reference potential. Connections from the conductive layer 38 to a reference potential can be accomplished by conductive epoxy, solder connection, clamped pressure creating a metal-to-metal contact, conductive gaskets or O-rings, or discrete drain wires.

Figure 6:
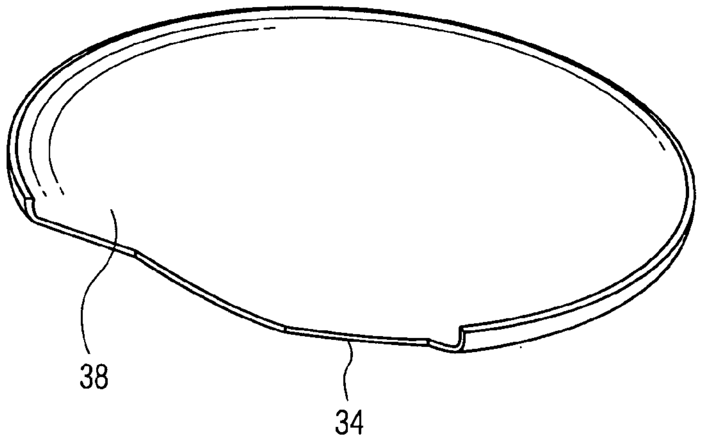
FIG. 6 illustrates a probe acoustic window cap which is constructed in accordance with the principles of the present invention.

FIG. 6 illustrates another embodiment of the present invention in which the acoustic window 34 is flat like a contact lens rather than dome-shaped. The plastic cap 34 is lined with a thin gold layer 38. An acoustic window of this form factor would be suitable for a moving transducer probe such as a multiplane TEE probe in which an array transducer is rotated around an axis normal to the plane of the array rather than oscillated back and forth.

Rather than use a continuous layer for the conductive layer 38, the shielding layer may also be formed as a grid-like screen or other porous pattern. Such a pattern can still provide effective EMI/RFI shielding but with enhanced transmissivity to ultrasound.

What is claimed is:

1. An ultrasound probe equipped with a mechanically oscillating transducer which is shielded from electromagnetic and radio frequency interference emissions comprising:

an ultrasonic transducer located in a fluid chamber containing fluid;

a movable mechanism on which the transducer is mounted for scanning of the transducer;

an acoustic window enclosing the fluid chamber through which ultrasonic energy is transmitted or received; and a shielding conductive layer directly lining the acoustic window which provides electromagnetic and radio frequency shielding of both the fluid chamber and the transducer on the movable mechanism within the fluid chamber and which is further coupled to a reference potential, wherein the fluid is directly located between the transducer on the movable mechanism and the shielding conductive layer.

2. The ultrasound probe of claim 1, wherein the conductive layer is located on the inner surface of the acoustic window.

3. The ultrasound probe of claim 1, wherein the conductive layer is embedded in the acoustic window.

4. The ultrasound probe of claim 1, wherein the acoustic window comprises a dome-shaped cap.

5. The ultrasound probe of claim 1, wherein the acoustic window comprises a relatively flat contact lens-shaped cap.

6. The ultrasound probe of claim 4, wherein the ultrasonic transducer comprises a curved array transducer which is oscillated to scan a volumetric region.

7. The ultrasound probe of claim 1, wherein the conductive layer is made of gold, a titanium/gold alloy, or aluminum.

8. The ultrasound probe of claim 1, wherein the conductive layer is formed on the acoustic window by vacuum deposition processes such as sputtering, vacuum evaporation, physical vapor deposition, arc vapor deposition, ion plating or laminating.

9. The ultrasound probe of claim 1, wherein the conductive layer is coupled to a reference potential by conductive epoxy, solder connection, clamped pressure creating a metal-to-metal contact, conductive gaskets or O-rings, or discrete drain wires.

10. The ultrasound probe of claim 1, wherein the conductive layer comprises a continuous layer of conductive material.

11. The ultrasound probe of claim 1, wherein the conductive layer comprises a porous layer of conductive material.

12. The ultrasound probe of claim 11, wherein the porous layer comprises a grid-like screen of conductive material.

13. The ultrasound probe of claim 1, wherein the conductive layer is thin enough to be highly transmissive of ultrasound at a frequency of the transducer.

14. The ultrasound probe of claim 13, wherein the conductive layer exhibits a thickness of 1/16 of a wavelength or less of the frequency of the transducer.

15. The ultrasound probe of claim 13, wherein the conductive layer exhibits a thickness in the range of 1000-3000 Angstroms.

* * * * *